United States Patent
Marie et al.

(10) Patent No.: US 6,765,985 B2
(45) Date of Patent: Jul. 20, 2004

(54) RADIOGRAPHIC APPARATUS AND IMAGED OBJECT SUPPORT THEREFOR

(75) Inventors: Alain Marie, Clamart (FR); Jean-Pierre Saladin, Bagneux (FR)

(73) Assignee: GME Medical Systems Global Technology Company LLC, Waukesha, WI (US)

( * ) Notice: Subject to any disclaimer, the term of this patent is extended or adjusted under 35 U.S.C. 154(b) by 0 days.

(21) Appl. No.: 10/150,137

(22) Filed: May 15, 2002

(65) Prior Publication Data

US 2003/0006387 A1 Jan. 9, 2003

(30) Foreign Application Priority Data

Jun. 6, 2001 (FR) .............................................. 01 07521

(51) Int. Cl.[7] .................................................. A61B 6/04
(52) U.S. Cl. ........................ 378/37; 378/177; 378/208
(58) Field of Search ........................... 378/37, 43, 177, 378/195, 196, 197, 208, 209

(56) References Cited

U.S. PATENT DOCUMENTS

| | | | | |
|---|---|---|---|---|
| 4,232,227 A | * | 11/1980 | Finkenzeller et al. | ....... 378/177 |
| 4,821,727 A | | 4/1989 | Levene et al. | ............... 128/653 |
| 5,018,176 A | * | 5/1991 | Romeas et al. | ............... 378/37 |
| 5,111,496 A | * | 5/1992 | Van Es et al. | ............... 378/177 |
| 5,177,778 A | * | 1/1993 | Tsurumaki et al. | .......... 378/117 |
| 5,189,686 A | * | 2/1993 | Hixson, Sr. | ................... 378/37 |
| 5,365,565 A | * | 11/1994 | Barbaric | ..................... 378/146 |
| 5,525,905 A | * | 6/1996 | Mohapatra et al. | .......... 324/318 |
| 5,553,111 A | * | 9/1996 | Moore et al. | ................... 378/37 |
| 5,715,292 A | * | 2/1998 | Sayag et al. | ............... 378/98.8 |
| 5,729,585 A | * | 3/1998 | Pellegrino et al. | ........... 378/154 |
| 6,041,097 A | * | 3/2000 | Roos et al. | .................... 378/62 |
| 6,175,117 B1 | | 1/2001 | Komardin et al. | ...... 250/363.06 |
| 6,304,627 B1 | * | 10/2001 | Horbaschek | ................. 378/19 |
| 6,382,832 B1 | * | 5/2002 | Schwieker et al. | .......... 378/196 |

FOREIGN PATENT DOCUMENTS

FR 2645006 10/1990

* cited by examiner

*Primary Examiner*—Edward J. Glick
*Assistant Examiner*—Allen C. Ho
(74) *Attorney, Agent, or Firm*—Jay L. Chaskin; Cantor Colburn LLP

(57) ABSTRACT

A radiographic apparatus comprises an image receiver and a source for delivering radiation towards the image receiver. Adjacent to the image receiver is a breast support with a body and a plate. The plate can be moved with respect to the body of the breast support, along the direction of propagation of the radiation. The movement of the plate of the breast support varies the position of the patient's breast in the path of the radiation thereby varying the magnification factor of the image.

28 Claims, 2 Drawing Sheets

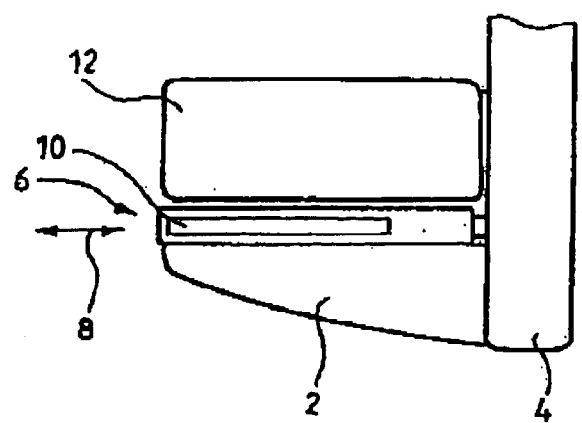
FIG_1
PRIOR ART
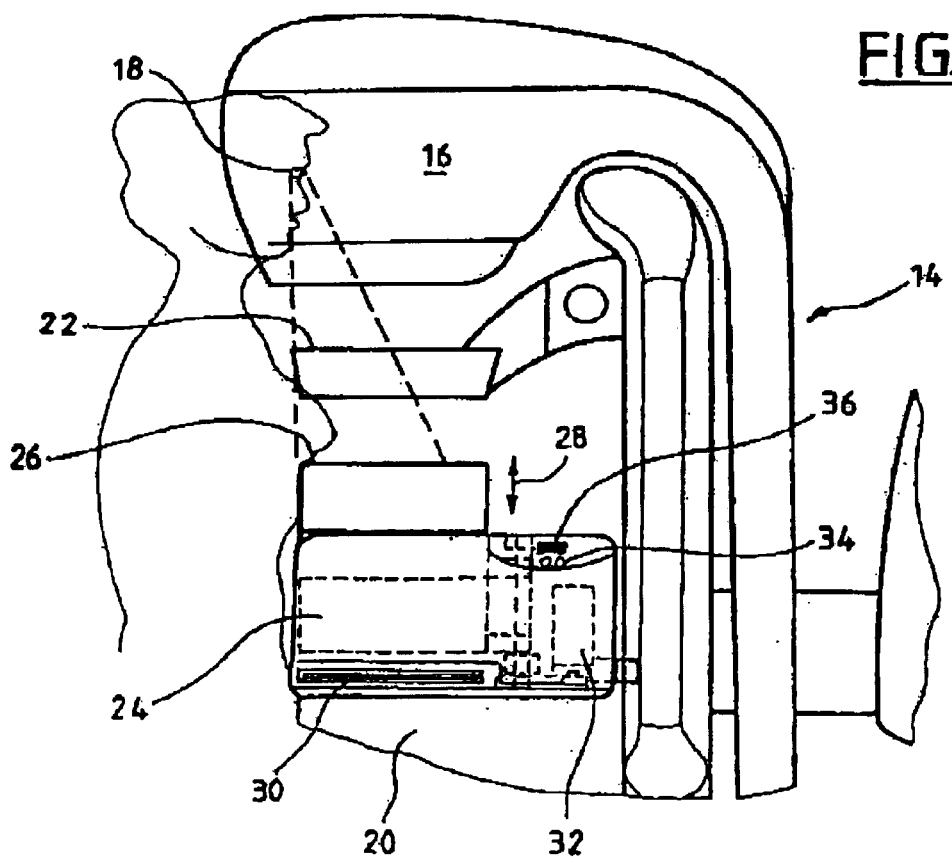
FIG_2

FIG_3
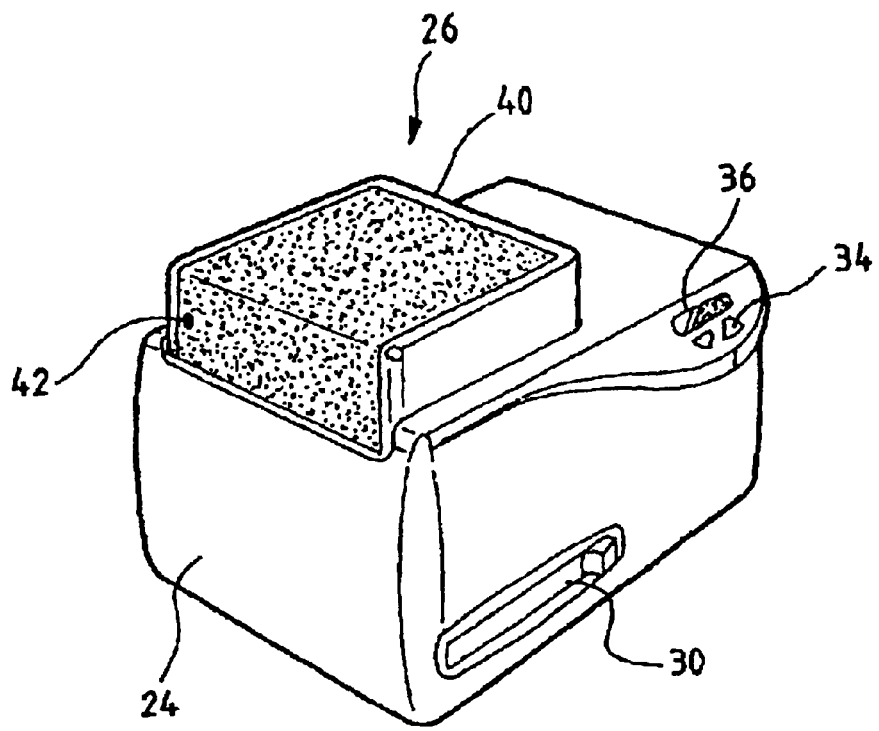
FIG_4
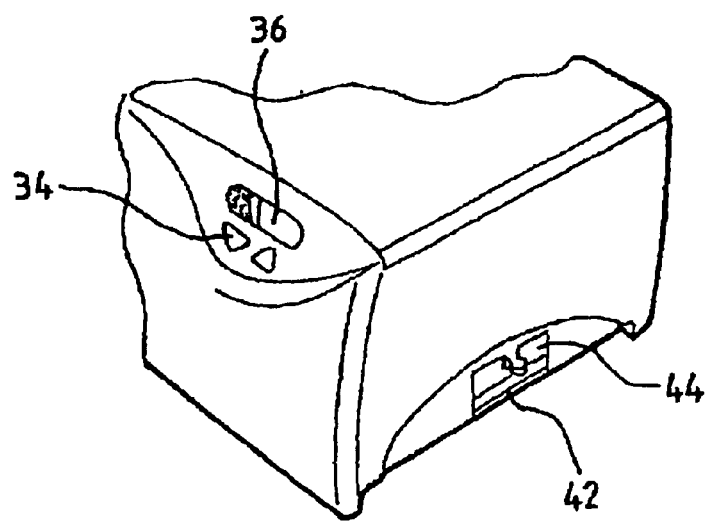

RADIOGRAPHIC APPARATUS AND IMAGED OBJECT SUPPORT THEREFOR

CROSS-REFERENCE TO RELATED APPLICATIONS

This application claims the benefit of a priority under 35 USC 119 to French Patent Application No. 01 07521 filed Jun. 6, 2001, the entire contents of which are hereby incorporated by reference.

BACKGROUND OF THE INVENTION

This invention relates to a radiographic apparatus to be used, for example, for mammography, and to a support for an object to be imaged by such an apparatus.

A mammography apparatus or mammographs are used for examining the breasts of a patient using X-rays. The image is acquired using an image receiver which may be in the form of a photographic plate or of a digital sensing means, GE Medical Systems Global Technology Company, LLC, has commercially available an analog or digital mammographs under the names Senographe 700T, Senographe 800T and Senographe 2000D. These mammographs apparatus have a vertical column on which an examination arm is mounted which can move up and down vertically. The examination arm has a source at its upper end that comprises the means for delivery of radiation, such as X-rays. The arm has means for receiving an image at its other end. A means for compression, such as a paddle, is slidably mounted on the arm, sliding in the direction of propagation of the radiation. This compression paddle allows the operator performing the examination to compress or maintain the breast being examined. The means for receiving an image comprises equipment allowing the radiation delivery to be controlled, notably a radiation measurement cell. In the case of a digital apparatus, the means for receiving comprises an image reception screen.

The means for image receiving has slideways on its top face for mounting means for stray radiation elimination. This means comprises a grid network formed of lead plates, parallel to the radiation, which can move with a translatory movement perpendicular to the direction of the radiation propagation. FIG. 1 is a partial diagrammatic view of the apparatus showing the means 2 for receiving, part of the examination arm 4, and this means 6.

More precisely, the means 6, which is commonly known by the names Bucky or Potter, has, at its lower part, means for sliding which cooperates with the slideways provided on the upper part of the means for image receiving to allow the means 6 to be mounted on the means for image receiving by sliding it in the direction of arrow 8. On its back part directed towards the examination arm 4, means 6 has electrical and mechanical connectors which fit to corresponding connectors provided on the examination arm. The connectors (not shown) provide electrical supply for driving the means 6. Additionally, the connectors ensure means 6 is held in position with respect to the means for image receiving. In the case of an analog apparatus, means 6 includes a slot 10 for inserting a cassette containing radiation sensitive film to be printed. Such a slot is not ordinarily provided in a digital apparatus.

When taking image at different degrees of magnification, means for magnification, such as a plate 12, is used. The magnification plate can be fixed onto examination arm 4 at two possible positions and comprises a material transparent to the radiation, at least in its part in the radiation path. The patient's breast rests on the upper platform of the magnification plate. Depending on the position of the plate, the breast is closer to or further from the radiation source and further from or nearer to the cassette containing the radiation sensitive film or the means for image receiving. Because of beam divergence, the various magnification positions consequently correspond to different degrees of magnification of the image of the breast. To change from one magnification factor to another, it is necessary to dismount or disconnect or remove or displace the magnification plate and dispose it at another position on the examination arm. Magnification factors are also limited by the number of positions for the magnification plate on the examination arm.

This known apparatus has the disadvantages of requiring several independent devices. Additionally, changing the magnification ratio involves dismounting and remounting the magnification plate. This complicates the operator's task and prolongs the duration of each examination. Magnification factors are also limited by the number of positions for the magnification plate on the examination arm.

BRIEF DESCRIPTION OF THE INVENTION

An embodiment of the invention is a radiograph apparatus that allows images to be taken with varying magnification factors in simple manner without requiring demounting and remounting operations to be performed on the apparatus.

In one embodiment of the invention, a radiographic apparatus has a source for delivering radiation towards a means for receiving an image, and means for supporting an object to be imaged, such as a breast, mounted adjacent to the means for receiving an image. The means for support comprises a body and plate that can be moved with respect to the body of the means for support. The plate is moved in the direction of propagation of the radiation and consequently allows the image enlargement to be varied.

In another embodiment of the invention, means for support of an object to be imaged, such as a breast, for a radiographic apparatus, has a body and a plate that can be moved with respect to the body. The plate is transparent to the radiation employed in the apparatus and can be moved with respect to the body in a direction substantially perpendicular to its surface.

BRIEF DESCRIPTION OF THE DRAWING

FIG. 1 is a partial diagrammatic side view of a prior art radiographic apparatus that may be used in mammography;

FIG. 2 is a side view in diagrammatic form of a radiographic apparatus according to an embodiment of the invention;

FIG. 3 is a perspective view in diagrammatic form of a means for support for the apparatus of FIG. 2; and FIG. 4 is a diagrammatic view in perspective of a means for support of the apparatus of FIG. 2.

DETAILED DESCRIPTION OF THE INVENTION

Referring to FIG. 2, there is shown a radiographic apparatus according to one embodiment of the invention, and showing apart from the apparatus, the outline of a patient. FIG. 2 is a side view of the apparatus configured for examination in the standing position for the taking of cranio-caudal images of the breast. The examination arm 14 having at its upper part, a source 16 comprising elements for delivering X-rays. The small circle 18 shows symbolically the position of the X-ray emission focus, the outer borders of the beam being shown in dashed lines. At its lower part, the examination arm has means 20 for receiving an image. The means for receiving an image comprises a measurement cell in the case of an analog apparatus and in a digital apparatus, the means for receiving an image comprises an image receiving screen FIG. 2 further shows a compression paddle 22 which can be moved up and down to compress the patient's breast during examination.

FIG. 2 shows means for support of the breast mounted on the means for receiving an image. The means for support comprises a body 24 and an upper plate 26 which can be moved with respect to the body in the direction of X-ray propagation, i.e., vertically as indicated by arrow 28 in FIG. 2. Plate 26 is designed to receive the patient's breast as shown in FIG. 2. Moving the plate with respect to the body 24 allows the degree of enlargement of the image of the patient's breast to be varied; for this, it is not necessary to move the body of the means 24 for support which stays in the same position with respect to the means for receiving an image. In the example, upper plate 26 is at its highest position corresponding to a magnification factor of two. In its lowest position, upper plate 26 is aligned with the top of body 24, which corresponds to a magnification factor of 1.5. The plate is movable in a direction perpendicular to its surface so as to always provide a flat support for the patient's breast.

As explained below, it is possible to allow continuous displacement of the upper plate 26 with respect to the body of the means 24 for support. The possibility of continuous movement allows continuous variation of the magnification factor and therefore possible values are no longer limited by the mounting position of the magnification plate on the examination arm. It is also possible to provide for the position of the upper plate to vary in a discrete fashion. In this case, the number of positions, i.e., the number of possible magnification ratios, can be chosen at will without the mounting position on the examination arm constituting a constraint.

In the example of FIG. 2, the means for support comprise an opening 30 in its lower portion that can receive a cassette containing the sensitive film. The apparatus is now an analog apparatus. The presence of the opening in the means for support enables only one single accessory to be used.

For the mounting of the means 24 for support, it is preferable to use a system of slideways and connectors as those used in the Bucky or Potter systems. This allows the means 24 for support to be used without modifying an existing apparatus. The means 24 for support consequently has one or more slideways on its lower side that allows it to be slidably mounted on the means 20 for receiving an image. The means 24 for support also has the connector described in FIG. 4, which ensures it is held against the examination arm and connected electrically thereto. The means 24 for support can also be fastened by other means, in the case of an apparatus not equipped with such a system of slideways and connectors.

The means for support can further comprise means for eliminating stray radiation, such as a movable grid. In this case, it is desirable to provide an electrical power connector for the drive of this grid.

FIG. 2 shows an example in which the upper plate of the means for support is driven by a motor 32. Motor 32 can be powered using the connectors that connect the support to the examination arm and is controlled by control members, in the present case, buttons 34. A display 36 may be further provided allowing the position of the upper plate to be displayed, by displaying the magnification factor. The upper plate could also be mechanically driven, with the mechanical position display, which may be provided in an apparatus not having a connector.

The apparatus in FIG. 2 operates as follows. Before starting the examination, the operator positions the means for support on the apparatus that is held in place by the connectors and the slideways. Using the control buttons 34, the operator adjusts the vertical position of the upper plate of the means for support. The operator can then introduce a cassette into the opening provided for this purpose (if used as an analog apparatus), if this was not done previously, and proceed to take the image. To take another image using a different magnification factor, the operator simply needs to adjust the vertical position of the upper plate without any need to dismount or disconnect or displace the means for support. A large number of adjustments positions are possible, thus allowing a more precise adjustment of magnification.

FIG. 3 is a diagrammatic view in perspective of the means for support of the apparatus of FIG. 2 showing the body 24 of the support, movable upper plate 26, opening 30 for a cassette (if used as an analog apparatus), control buttons 34 and display 36. In the example, the upper movable plate is supported by a U-shaped frame 40 that can be opaque to X-rays. The walls of the frame extend vertically; the frame is open towards the patient or, in other words, its base is directed towards the examination arm. This helps to ensure the examination region is kept as free as possible. The upper plate extends between the arms of the frame, and is transparent to X-rays. This can be a carbon fiber web about one millimeter thick, secured between the arms of the frame. FIG. 3 also shows the arms of the frame connected by a vertical wall 42 that is also transparent to X-rays. This wall protects the drive members contained inside the means for support and avoids the possibility of trapping when upper plate 26 descends.

To provide the movement of the plate and frame, the frame can be mounted for translatory movement on vertical guide columns via rolling bearing or the like. A threaded member is then provided in the frame engaging with an endless screw parallel to the guide columns, rotatively mounted in the means for support of the breast. Rotation of the screw, which can be manual or motor-driven, causes the frame and the plate to move up or down. The guide columns may be mounted on the bottom of the U-shaped frame or on the sides thereof to avoid any interference with the X-rays and withstands the compression force exercised by the compression paddle. Use of an endless screw for positioning allows accurate vertical positioning of the upper plate. Additionally, it ensures irreversibility of the drive while resisting the compression force. Continuous adjustment of the vertical position of the plate can be provided for or, alternatively, adjustment to a finite number of set positions. The choice of the number of positions is only limited by the length of travel of the plate.

FIG. 4 is a partial view in perspective of the means for support of the apparatus of FIG. 2. FIG. 4 shows that part of the means for support that comes into contact with the examination arm. The connector with pins 42 provide electrical contact, together with the mechanical locking system 44 ensuring that the means for support is held in place. Mechanical connector 44 can mate with a corresponding connector on the examination arm. The electrical connector formed by the pins 42 can mate with a corresponding electrical connector on the examination arm. The mechanical and electrical connectors are provided on the rear side of the means for support, i.e., the side adjacent the side on which the moveable plate extends. This allows a connection with the examination arm.

Typical dimensions of he means for support are as follows: length (horizontally as seen in FIG. 2): 35 cm; width (perpendicularly to the plane of FIG. 2): 30 cm; thickness (vertically in the view of FIG. 2): 20 cm; plate length: 30 cm; plate width: 25 cm; and amount of vertical travel of the plate: 13 cm.

These dimensions allow cassettes to be used with standardized film dimensions. The length of travel ensures magnification can be varied between a factor of 1.5 and a factor of 2.

The apparatus has at least one of the following advantages. Regardless of the magnification factor required, just one means for support is mounted on the examination arm. In order to change from one magnification factor to another it is not necessary to remove, dismount or displace the means for support and then fit it again at a different position. The time required to change the magnification factor is therefore reduced.

Various modifications in structure and/or function and/or steps may be made by one skilled in the art without departing from the scope and extent of the disclosed embodiments of the invention.

What is claimed is:

1. A radiographic apparatus comprising:
  a. means for receiving an image;
  b. means for providing a source of radiation towards the means for receiving an image;
  c. means for supporting an object to be imaged;
  d. the means for supporting an object being mounted adjacent to the means for receiving an image;
  e. the means for supporting an object comprising a body and a plate movable with respect to the body in a direction of propagation of the radiation; and
  f. the means for support is mounted for translatory movement on the means for receiving an image.

2. The apparatus according to claim 1 wherein the means for support comprises an opening for receiving a cassette.

3. The apparatus according to claim 2 wherein the means for support comprises means for eliminating stray radiation.

4. The apparatus according to claim 2 wherein the means for support comprises a drive for the movable plate.

5. The apparatus according to claim 1 wherein the means for support comprises means for eliminating my radiation.

6. The apparatus according to claim 5 wherein the means for support comprises a drive for the movable plate.

7. The apparatus according to claim 1 wherein the means for support comprises a drive for the movable plate.

8. The apparatus according to claim 7 wherein the means for support comprise control members for the position of the moveable plate.

9. The apparatus according to claim 1 wherein the means for support comprises means for display.

10. The apparatus according to claim 1 comprising:
  a. an examination arm supporting the means for receiving an image;
  b. the arm having a mechanical connector; and
  c. the means for support having a mechanical connector that mates with the mechanical connector of the examination arm.

11. The apparatus according to claim 1 comprising:
  a. an examination arm supporting the means for receiving an image;
  b. the arm having an electrical connector; and
  c. the means for support having an electrical connector that mates with the electrical connector of the examination arm.

12. The apparatus according to claim 1 wherein the body is fixed with respect to the means for receiving an image.

13. A means for support for a radiography apparatus comprising:
  a. a body;
  b. a plate transparent to radiation;
  c. the plate being movable with respect to the body in a direction substantially perpendicular to a surface thereof; and
  d. the body and the plate mounted for translatory movement on a means for receiving an image.

14. The means for support according to claim 13 comprising:
  an opening for receiving a cassette.

15. The means for support according to claim 14 comprising:
  means for eliminating stray radiation movable in a direction substantially parallel to the surface of the moveable plate.

16. The means for support according to claim 13 comprising:
  means for eliminating stray radiation movable in a direction substantially parallel to the surface of the moveable plate.

17. The means for support according to claim 13 comprising:
  means for driving the moveable plate.

18. The means for support according to claim 17 comprising:
  control members for the position of the moveable plate.

19. The means for support according to claim 13 comprising:
  means for display for indicating the position of the moveable plate.

20. The means for support according to claim 13 comprising:
  a mechanical connector on a face thereof adjacent to a face of the moveable plate.

21. The means for support according to claim 13 comprising:
  an electrical connector on the face thereof adjacent to a face of the moveable plate.

22. A radiographic apparatus comprising:
  a. means for providing a source of radiation;
  b. means for providing an image of an object as a result of the means for providing a source of radiation;
  c. means for magnification of the image;
  d. the means for magnification comprising:
    (1) a body;
    (2) a plate moveable with respect to the body in a direction of emission of the radiation;
  (e) the movable plate being supported by a frame that is opaque to the radiation; and
  (f) arms of the frame being connected by a vertical wall transparent to the radiation.

23. The apparatus according to claim 22 wherein the means for magnification is moveable to a selected position in the direction of the radiation.

24. The apparatus according to claim 22 wherein the means for magnification is moveable for magnification factor in the range of 1.5 to 2.

25. The apparatus according to claim 22 wherein the means for magnification is continuously moveable.

26. The apparatus according to claim 22 comprising:
means for displaying a magnification factor.

27. The apparatus according to claim 22 wherein the movable plate is transparent to the radiation.

28. The apparatus according to claim 22 wherein the body is fixed with respect to the means for providing an image.

* * * * *